United States Patent [19]

Weber et al.

[11] Patent Number: 5,154,915

[45] Date of Patent: Oct. 13, 1992

[54] DENTIFRICES CONTAINING AMINOALKYL SILICONES AND SARCOSINATE SURFACTANTS

[75] Inventors: Thomas R. Weber, Fairlawn, N.J.; Nancy H. Krysiak, Ridgfield, Conn.; John P. Viccaro, Whitestone, N.Y.; Samuel Lin, Paramus, N.J.; Todd Domke, Clifton, N.Y.

[73] Assignee: Chesebrough-Pond's USA Co., Division of Conopco, Inc., Greenwich, Conn.

[21] Appl. No.: 513,055

[22] Filed: Apr. 23, 1990

Related U.S. Application Data

[63] Continuation of Ser. No. 426,477, Oct. 23, 1989, abandoned, which is a continuation of Ser. No. 276,973, Nov. 28, 1988, abandoned.

[51] Int. Cl.$^5$ .................. A61K 7/16; A61K 7/18; A61K 7/22
[52] U.S. Cl. .................. 424/54; 424/49; 424/52
[58] Field of Search .................. 424/49-58

[56]     References Cited

U.S. PATENT DOCUMENTS

| | | | |
|---|---|---|---|
| 2,806,814 | 9/1957 | Richter | 424/49 |
| 3,032,577 | 5/1962 | Morehouse | 260/448.2 |
| 3,389,160 | 6/1968 | Reid | 260/448.2 |
| 3,402,191 | 9/1968 | Morehouse | 260/448.2 |
| 3,507,955 | 4/1970 | Osipow | 424/54 |
| 3,624,120 | 12/1969 | Yetter | 260/448.2 |
| 3,852,075 | 12/1974 | Basador | 106/11 |
| 3,860,709 | 1/1975 | Abbott et al. | 424/184 |
| 4,071,614 | 1/1978 | Grimm | 424/49 |
| 4,161,518 | 7/1979 | Wen et al. | 424/52 |
| 4,213,961 | 7/1980 | Curtis et al. | 424/54 |
| 4,243,658 | 1/1981 | Chang | 424/52 |
| 4,246,029 | 1/1981 | Sanders et al. | 106/3 |
| 4,256,731 | 3/1981 | Curtis et al. | 424/54 |
| 4,304,766 | 12/1981 | Chang | 424/52 |
| 4,430,235 | 2/1984 | Chu et al. | 252/49.6 |
| 4,450,152 | 5/1984 | Ona et al. | 424/70 |
| 4,454,110 | 6/1984 | Zeslafsk et al. | 424/54 |
| 4,485,090 | 11/1984 | Chang | 424/52 |
| 4,507,455 | 3/1985 | Tangney et al. | 528/26 |
| 4,510,127 | 4/1985 | Chang | 424/49 |
| 4,544,498 | 12/1970 | Holdstock et al. | 260/29.2 |
| 4,680,366 | 7/1987 | Tanaka | 528/27 |
| 4,994,593 | 2/1991 | Lin et al. | 556/424 |
| 5,078,988 | 1/1992 | Lin et al. | 424/54 |

FOREIGN PATENT DOCUMENTS

| | | |
|---|---|---|
| 689679 | 1/1953 | United Kingdom . |
| 1194885 | 6/1970 | United Kingdom . |
| 1447254 | 8/1976 | United Kingdom . |

OTHER PUBLICATIONS

Chemical Abstracts; vol. 90; No. 16; 16 Apr. 1979; p. 612.

Seifen-Ole-Fette-Wachse, vol. 114, No. 2, 4th Feb. 1988, Augsburg, DE, pp. 51-54.

Primary Examiner—Shep K. Rose
Attorney, Agent, or Firm—Gerard J. McGowan, Jr.

[57]     ABSTRACT

Dentifrices, including toothpastes and mouthwashes, are provided which include aminoalkyl silicones and sarcosine surfactants. In the mouth, the aminoalkyl silicones form a lasting hydrophobic film on the teeth for prevention of cavities and stain. Antimicrobial compounds such as chlorhexidine may be included.

35 Claims, No Drawings

DENTIFRICES CONTAINING AMINOALKYL SILICONES AND SARCOSINATE SURFACTANTS

This is a continuation application of Ser. No. 426,477, filed Oct. 23, 1989; which, in turn, is a continuation of Ser. No. 276,973, filed Nov. 28, 1988 both now abandoned.

BACKGROUND OF THE INVENTION

Great strides have been made in recent years in the field of oral health care. However, much remains to be done. While the development of anticaries agents, especially the fluorides, has led to a decline in the incidence of tooth caries it is desirable to even further decrease the number of teeth affected thereby. Moreover, attention in the oral health care field has increasingly focused on the problems of gum disease, periodontitis. While the antibacterial agents have been proposed for inclusion in products for use by consumers in the treatment of periodontitis, certain problems have been associated with their use. For example, use of chlorhexidine, which has been known as antibacterial agent, has been associated with staining problems. It produces yellow to dark brown stains on teeth, tongue and oral mucosa. Furthermore, chlorhexidine has a very bitter taste.

There has been a need, therefore, for dentifrices which will prevent staining of antibacterial agents, and which have an improved taste. Moreover, dentifrices having improved anticaries effects are also desirable.

Staining can be troublesome, whether or not chlorhexidine is the cause. The accumulation of stains on tooth surfaces poses an esthetic problem for many individuals. Stains are usually extrinsic in nature and generally represent discolorations of the pellicle and/or plaque. The exact mechanisms involved in stain formation are still obscure. It has been suggested that pigments produced by chromagenic bacteria, colored products from the chemical transformation of pellicle components and adsorption/retention of dietary constituents contribute to extrinsic stain formation. The dietary factors which appear to contribute heavily to stain accumulation include coffee, tea, and red wines, as well as smoking. In addition to chlorhexidine, staining is promoted by other cationic antimicrobial agents such as hexetidine or quaternary ammonium compounds.

Plaque is a common factor in caries, gum disease and staining and greatly contributes to their development. Proper oral hygiene as current practiced requires that plaque be removed or prevented not only for cosmetic purposes but also to eliminate a source of potential injury to teeth and gums.

Silicones have previously been suggested for inclusion in dentifrice compositions in that it has been expected that they would coat the teeth and thereby prevent caries and staining. For example, British Patent Specification 689,679 discloses a mouthwash containing an organopolysiloxane for the purpose of preventing adhesion of, or for removal of, tars, stains, tartar and food particles from the teeth. However, polymers such as those disclosed in the '679 specification, have not generally been successfully used for coating the teeth since it has been found that the polysiloxane does not adhere to the teeth for prolonged periods of time. Therefore, the need for dentifrice formulations including a hydrophobic substance which effectively coats the teeth has not been satisfied.

Yetter U.S. Pat. No. 3,624,120 discloses quaternary ammonium salts of cyclic siloxane polymers which are said to be useful as cationic surfactants, as bactericides and as anticariogenic agents. Yetter indicates that it is believed that the siloxane polymer absorbs on calcium phosphate to form a film which decreases the rate of acid solubilization. However, due to the solubility of the cyclic, surface active, low molecular weight, high N/Si ratio compounds of Yetter, it would not be expected that they could impart of lasting, strongly hydrophobic film to the surface of teeth. Moreover, there does not appear to be any disclosure in Yetter that its low molecular weight compounds would have any usefulness in preventing staining. Other problems with the Yetter compounds are their high cost due to the high N/Si ratio. Also, the freedom from toxicity of high N/Si compounds may be questioned.

Viccaro, et al. copending application Ser. No. 276,704 filed simultaneously herewith and entitled "Dentifrice Containing Aminoalkyl Silicones" discloses dentifrice formulations including aminoalkyl silicones for coating the teeth and inhibiting stain and caries. The aminoalkylsilicones have been found to be more substantive than alkylsilicones, apparently due to the interaction of the positively charged nitrogen of the amine with the negative charges on the surfaces of the teeth. However, dentifrices often include an anionic surfactant and the positive charges on the amino groups are believed to be complex with the negative charge on the anionic surfactant thereby eliminating or reducing the aforementioned advantages of the cationic amino groups.

Richter, U.S. Pat. No. 2,806,814 discloses dentifrices which include sodium N-lauroyl sarcoside or N-lauroyl sarcosine and organopolysiloxanes. The sarcosides are said to inhibit the acid producing effects of bacteria in saliva while the silicones are said to improve the antibacterial and acid inhibiting activity thereof. Dimethyl siloxanes and polysiloxanes having one aliphatic and one aromatic group are disclosed.

The abstract of Japanese Patent No. J 60085422A discloses toothpastes containing silicon-type polishing agents, 0.05-5% N-alkoyloyl sarcosinate and 1-1000 ppm chlorhexidine salt. The toothpaste is said to lessen mouth odor.

SUMMARY OF THE INVENTION

Applicants have discovered dentifrices which include aminoalkyl silicones and sarcosinate surfactants which form a hydrophobic barrier on the surface of teeth useful in preventing staining of teeth and in prevent caries. The antistaining properties of the dentifrices of the invention are of particular interest when the compositions of the invention are used to conjunction with antimicrobials which have a tendency to stain. The antistaining properties of the aminoalkyl silicones may likewise be of use when other staining compounds, such as stannous fluoride are included in the dentifrices. In a preferred embodiment, the aminoalkyl silicones comprise amodimethicones. Also preferred are compounds having a molecular weight of about 5,000 and above and compounds which are non-cyclic.

The aminoalkyl silicones included in the dentifrices of the invention comprise two basic units, $$R^1{}_m R_n SiO_{(4-m-n)} \qquad (1)$$

wherein $1 \leq m+n \leq 3$, $1 \leq n \leq 3$, $0 \leq m \leq 2$, where m and n are integers, and preferably m=1, n=1, and $$R^1_a R^2_b SiO_{(4-a-b)/2} \quad (2)$$

wherein $1 \leq a+b \leq 3$, wherein a and b are integers and wherein $R^1$ and $R^2$ are hydrocarbons or fluorinated hydrocarbons of 1 to 10 carbon atoms, hydroxy, alkoxy, hydrogen, acetoxy or cyanoalkyl such as cyanopropyl and R is $$-R^3-N\begin{matrix}R^4\\|\\R^5\end{matrix} \text{ or } -R^3-\overset{R^4}{\underset{R^6}{N^+}}-R^5 \ X^-$$

wherein $R^3$ is a divalent alkylene of 1 to 20 carbons, optionally including O atoms, $R^4$, $R^5$ and $R^6$ may be different or the same and are selected from the group consisting of H, hydrocarbons of 1 to 20 carbons, and hydrocarbons of 1 to 20 carbons containing N and/or O atoms, preferably where the nitrogens are present as aliphatic amines and the oxygen atoms are present in hydroxyl groups, and $X^-$ is an anion preferably is selected from the group consisting of halide, hydroxide, tosylate and other monovalent anions. The amino alkyl silicones of the invention include 60% or fewer, by repeat unit, of unit (1). The aminoalkyl silicones of the invention may be linear, branched, random or block copolymers. The above-defined aminoalkyl silicones when used in a dentifrice provide a hydrophobic film for the teeth which yields antistain and anticaries benefits.

The silicones of the invention have 60% or fewer repeat units of formula 1, more preferably 30% or fewer in order to combine acceptable substantivity of the film with modes cost and the absence of discoloration and bitter taste which tend to characterize amino silicones having high charge density.

Sarcosine surfactants are generally salts of N-acylsarcosinates, although N-acylsarcosines may also be useful and are within the scope or the present invention. There may be from 7 to 21 carbon atoms in the acyl moiety. The sarcosine surfactants are of the formula $R^{15}CON(CH_3)CH_2CO_2Q$ wherein R is a hydrocarbon group of from 8 to 22 carbon atoms and Q is selected from the group consisting of cations, preferably alkali metal ions and ammonium ions, and hydrogen.

A particularly useful embodiment of the invention is a dentifrice which comprises a mixture of (I) an organosiloxane polymer which includes:
(a) at least one unit of formula 3, $$R^{11}-\overset{R^{10}}{\underset{R^9}{N}}-(CH_2CH_2N)_n-R^8-\overset{|}{\underset{R^7_a}{Si}}O_{(3-a)/2} \quad (3)$$

wherein:
a is from 0–2 and n is from 0–5,
$R^7$ is a monovalent radical,
$R^8$ is a divalent hydrocarbon radical,
$R^9$, $R^{10}$, and $R^{11}$ may be the same or different and are selected from the group consisting of H, $$-CH_2-CH-R^{12}, \text{ and } R^{12},$$
$$\phantom{-CH_2-CH}|\phantom{R^{12}, \text{ and } R^{12}}$$
$$\phantom{-CH_2-CH}OH$$

where $R^{12}$ is a monovalent hydrocarbon or hydrogen, and (b) at least one unit of formula 4, $$R_a^{13}R_c^{14}SiO_{(4-a-c)/2} \quad (4)$$

wherein $R^{13}$ and $R^{14}$ are the same or different monovalent radicals, a and c are integers selected from the group 0, 1, 2 and 3, and a plus c is 0, 1, 2 or 3, (II) an orally acceptable antimicrobial compound other than (I), such as chlorhexidine, and (III) a sarcosine surfactant of the formula $R^{15}CON(CH_3)CH_2CO_2Q$ wherein $R^{15}$ is a hydrocarbyl moiety of 7 to 21 carbon atoms and Q is a cation, preferably an alkali metal cation or ammonium cation, or hydrogen. It is preferred that 60% or fewer repeat units of Formula 3, preferably 30% or fewer, are present in the molecule.

Although applicants do not wish to be limited to any particular theory of operation of their invention, it is believed that when the aminoalkyl silicones come in contact with water of an appropriate pH, the nitrogens are protonated and the cations so formed are attracted to the negatively charged phosphate ions on the teeth. The hydrophilic charged moieties of the aminoalkyl silicones thus attracted to the teeth act as anchors for the hydrophobic alkyl silicone film which is thereby deposited onto the teeth and protects them from stain and caries. The chlorhexidine- or other antimicrobial-containing dentifrice is useful in that antimicrobials such as chlorhexidine and cetylpyridmium chloride which are positively charged in the dentifrice formulation appear to enhance the deposition of the silicones, although their antimicrobial activity may be negated. It is believed that the positive charges of the antimicrobials interact with the negative charge in the sarcosinate to permit enhanced deposition of the silicone. Also, inclusion of the aminoalkyl silicones permits use of such antimicrobials with reduced staining.

The dentifrice of the invention can take several forms. It may, for instance, be a toothpaste cream or gel, or oral spray or it may comprise a mouthwash. In its preferred embodiment, the aminofunctional silicone of the invention (whether amodimethicones or other amino alkyl silicones,) is present in the form of an emulsion. As indicated above, in a particularly preferred embodiment of the invention, an antimicrobial agent which assumes a positive charge in the formulation such as a quaternary ammonium salt or a bis boguanide such as chlorhexidine, is included in the dentifrice together with the aminofunctional silicone. Typical dentifrice ingredients may be included, depending, of course, on the form of the dentifrice. Toothpastes and gels will generally include surfactant, one or more abrasives and may include humectants. Mouthwashes will generally include alcohol, water and humectant. The dentifrice may also take the form of a denture cleaner. In accordance with a further embodiment of the invention, mouthwashes are provided which include amino alkyl silicones.

It is believed that the compositions of the invention including an antimicrobial may be useful in prevention of gum disease by reducing or preventing plaque. Indeed, as indicated above, plaque is a common factor in caries, gum disease and staining and greatly contributes to the development of each of these problems.

It is our view that the positively charged nitrogen-containing silicones of the invention are attracted to negatively charged surfaces such as enamel so that silicones including alkyl amine groups are more substantive to the surface of the teeth. Moreover, increasing the number of aminoalkyl groups per molecule enhances the substantivity of the silicone. The increased substantivity of aminoalkyl-containing silicones enables them to impart a durable water repellent barrier to enamel. The substantivity of the silicones is increased by cationic antimicrobial agents, although their antimicrobial effects may be negated by the negatively charged sarcosinates. Aminoalkyl silicones do not adversely affect the antiplaque activity of quats and/or bisbiquanides. On the other hand, while increasing the number of aminoalkyl groups per molecule should improve the association of the molecule with the surface of the tooth, it also tends to increase the solubility and reduce the hydrophobicity of the polymer. Consequently, it is preferred that the aminoalkyl groups constitute from 5 to 30% by repeat unit of the polymer. In other words, it is preferred that the number of silicon atoms which have nitrogen-containing moieties appended thereto constitute from 5 to 30% of the total number of silicon atoms.

While it is expected that the film of the alkylamino silicones will prevent the adhesion of staining materials such as chlorhexidine it is also believed that removal of such staining materials from the teeth will be facilitated thereby. Insofar as the dentifrices of the invention can reduce staining they would also provide a cosmetic as well as a health benefit. It is also contemplated that the compositions of the invention will reduce pain and progression of root caries via the coating action and will reduce unpleasant tastes from dental product components such as antimicrobials and surfactants, and will prevent calculus growth. Moreover, coating of hypersensitive area may result in desensitization, etc.

The aminoalkyl silicones may be incorporated into dentifrices as oils as well as emulsions, but preferably as emulsions. The present invention also encompasses the process of applying the aminoalkyl silicones described herein onto the teeth, particularly in as the emulsion. Particularly preferred is the process of applying the amino alkyl silicones onto the teeth followed by application of chlorhexidine or other antimicrobials in another dentifrice, such as a mouthwash as this will tend to minimize the loss of antimicrobial properties.

A preferred class of aminoalkyl silicones are the amodimethicones.

DETAILED DESCRIPTION OF THE INVENTION

The dentifrices of the invention preferably contain from 0.1 to 20% by weight, preferably 0.5 to 10% and even more preferably from 0.5% to 2% by weight of the aminoalkyl silicones of the invention and a sarcosine surfactant preferably from 0.5 to 6%, especially 0.5 to 1.5% by weight. Total surfactant including the sarcosine surfactant may comprise from 0.1 to 15% by weight, preferably from 0.5 to 10%. The ratio (w/w) of the sarcosine surfactant to the aminoalkyl silicone should be between 0.1:1 and 1.5:1, preferably between 0.2:1 and 1.2:1 and more preferably between 0.3:1 and 0.7:1. The aminoalkyl silicones of the invention are generally non-cyclic, and comprise two basic units of formulas 1 and 2, respectively, and may be linear, branched, random or block copolymers. Formulas 1 and 2 are as follows:

$$R^1{}_m R_n SiO_{(4-m-n)/2} \quad (1)$$

wherein $1 \leq m+n \leq 3$, $1 \leq n \leq 3$, $0 \leq m \leq 2$, where m and n are integers, preferably $m=1$, $n=1$ and $$R^1{}_a R^2{}_b SiO_{(4-a-b)/2} \quad (2)$$

wherein $1 \leq a+b \leq 3$, a and b are integers, and wherein $R^1$ and $R^2$ are preferably hydrocarbons or fluorinated hydrocarbons of 1 to 10, even more preferably 1 to 4, carbon atoms. Examples include methyl, ethyl, phenyl, vinyl, and trifluoropropyl. Methyl and phenyl are preferred. $R^1$ and $R^2$ may be cyanoalkyl (preferably cyano-$C_1$ to $C_6$ alkyl), such as cyanopropyl. $R^1$ and $R^2$ may also be hydroxyl, alkoxy, hydrogen, acetoxy or other reactive groups but their amounts are preferred to be low in order to promote adequate shelf stability. R is defined as $$-R^3-N-R^5 \text{ or } -R^3-\overset{+}{N}-R^5 \ X^-$$
$$\qquad |\qquad\qquad\qquad |$$
$$\qquad R^4\qquad\qquad\qquad R^4$$
$$\qquad\qquad\qquad\qquad\qquad R^6$$

wherein $R^3$ is a divalent alkylene of 1 to 20 carbons optionally including 0 atoms, preferably 3 to 5 carbons. $R^4$, $R^5$ and $R^6$ may be different or the same and are H, hydrocarbons of 1 to 20 carbons, and hydrocarbons of 1 to 20 carbons containing N and/or 0 atoms. $R^4$, $R^5$ and $R^6$ preferably containing 1 to 10, even more preferably 1 to 4 carbon atoms. Examples are methyl, ethyl and phenyl. X- is an anion preferably selected from the group consisting of halide, hydroxide, tosylate and other monovalent anions. Examples of R include:

$-(CH_2)_3-NH_2, -(CH_2)_3-NHCH_2CH_2CH_3,$ $\qquad\qquad\qquad\qquad OH$
$\qquad\qquad\qquad\qquad |$
$-(CH_2)_3-O-CH_2-CH-CH_2-NH_2,$ $\qquad\qquad\qquad\qquad\qquad\qquad Cl^-$
$-(CH_2)_3-\overset{+}{N}H_3Cl^-, -(CH_2)_3-\overset{+}{N}(CH_3)_2(C_{18}H_{37}),$ $-(CH_2)_3-\overset{+}{N}H_3OH^- \text{ and } -(CH_2)_3-N(CH_2CH_2OH)_2.$ The concentration of formula (1) in the aminoalkyl siloxane polymer may range from 1% to 99% by repeat units, preferably from 1 to 60%, more preferably from 5 to 30%, and even more preferably from 5 to 10%. The preferred minimum molecular weight of the aminoalkyl silicone of the invention is 5,000. It is desirable that the molecular weight of the aminosilicones compounds be about 5,000 or greater since below 5,000 cyclization may occur and the compounds may dissolve in water. It is believed important that the silicones not be cyclized and not be soluble in order to permit them to deposit a lasting film onto the teeth. If the compounds are unduly soluble in water, it is believed that the film will too readily wash off the teeth.

There is not theoretical ceiling on the molecular weights of the silicones so long as they spread onto tooth enamel by brushing action or rinsing. Molecular weights will tend to fall within the range of 5,000 to 100,000, preferably 5,000 to 30,000. However, molecular weights may range as high as 1,000,000 or more. Compounds with molecular weight from 10,000 to 30,000 would be expected to yield more substantive films than compounds having lower molecular weights. High molecular weight silicones are believed to form more stable films on the enamel surface whereas silicones of lower molecular weights tend to spread faster. Particularly preferred are dentifrices having average molecular weights of amino alkyl siloxane polymers in the ranges above. Silicones of high and low molecular weights may be mixed together to obtain mixtures of the desired viscosity. A viscosity for the aminoalkyl silicone in the range of 50 cps to 3,000 cps is preferred.

In the preferred embodiment the dentifrice preferably comprises a mixture including (I) from 0.01% to 20% by weight, even more preferably from 0.5% to 5% by weight of an organosiloxane polymer which includes:

(a) at least one unit of formula 3,

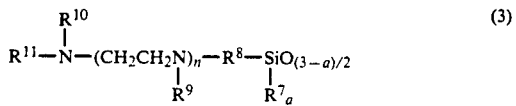

wherein:
a is from 0–2 and n is from 0–5,
$R^7$ is a monovalent radical,
$R^8$ is a divalent hydrocarbon radical,
$R^9$, $R^{10}$, and $R^{11}$ may be the same or different and are selected from the group consisting of H,

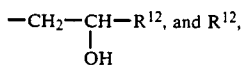

where $R^{12}$ is a monovalent hydrocarbon radical or hydrogen, and (b) at least one unit of formula 4,

wherein $R^{13}$ and $R^{14}$ are the same or different monovalent radicals, a and c are integers selected from the group of 0, 1, 2 and 3 and a plus c is 0, 1, 2 or 3, (II) from 0.001% to 3%, more preferably from 0.1 to 1% by weight of an orally acceptable antibacterial compound, such as a quaternary ammonium compound other than (I) or a bis biguanide such as chlorhexidine, and (III) a sarcosine surfactant of the formula $R^{15}CON(CH_3)CH_2CO_2Q$ wherein $R^{15}$ is a hydrocarbyl moiety of 8 to 22 carbon atoms and Q is a cation, preferably alkali metal cation or ammonium cation, or is hydrogen.

Each $R^7$ may independently be a hydrocarbon radical, a halogenated hydrocarbon radical, hydrogen, hydroxyl or alkenyl. Preferably, $R^7$ comprises from 1 to 10 and especially 1 to 4 carbon atoms. Examples of $R^7$ are methyl, phenyl or -trifluoropropyl.

Each $R^8$ independently preferably comprises a divalent hydrocarbon radical having 3 or more carbons. Examples are propylene and butylene. Preferably $R^8$ does not exceed 10 carbon atoms.

$R^{12}$ is preferably selected from the group consisting of hydrogen, methyl or phenyl. Preferably $R^{12}$ includes 10 or fewer carbon atoms, more preferably, 4 or fewer.

Preferably $R^{13}$ and $R^{14}$ are independently selected from the group consisting of hydrocarbon radicals, halogenated hydrocarbons, hydrogen, hydroxyl, cyanoalkyl (preferably cyano $C_1$–$C_6$ alkyl) such as cyanopropyl and alkoxyls. It is preferred that $R^{13}$ and $R^{14}$ include from 1 to 10, preferably from 1 to 4 carbon atoms. Especially preferred $R^{13}$ and $R^{14}$ groupings are independently selected from the group consisting of methyl, phenyl and -trifluoropropyl.

Preferably a plus c is equal to 2.

Preferred sarcosine surfactants include sodium N-lauroyl sarcosinate (Hamposyl L-30, ex Grace), sodium N-cocoyl sarcosinate (Hamposyl C-30, ex Grace), and sodium N-myristoyl sarcosinate (Hamposyl M-30, ex Grace). N-acyl sarcosinates are prepared from a fatty acid chloride and sarcosine: $R^{15}COCl + CH_3NHCH_2CO_2Na + NaOH \rightarrow R^{15}CON(CH_3)CH_2CO_2Na + NaCl + H_2O$. Preferably Q is $Na^+$, $K^+$ or $NH_4^+ \cdot R^{15}$ preferably has from 9 to 13 carbon atoms.

The preferred antibacterial compound is chlorhexidine. Other include hexetidine, alexidine, quaternary ammonium antibacterial compounds and metal ion-containing antibacterial compounds mentioned later herein. The "quats" usually include a quaternary ammonium group having at least one long chain or carbon atoms attached thereto. The organopolysiloxane polymer comprising at least one unit of Formula 3 and one unit of Formula 4 may be used in a dentifrice according to the invention with or without the antibacterial compound.

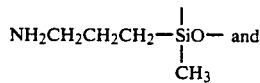

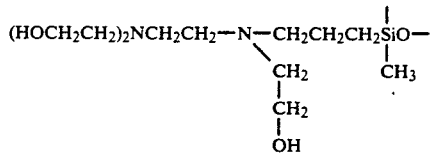

The content of Formula 3 in the polymer ranges from 0.5% and up to 60% by repeat unit, preferably between 1 and 30%, more preferably from 5 to 15% by repeat unit. For reasons given above, the molecular weight is preferably above about 5,000.

The molecular weight of the preferred compound is preferably between 5,000 and 100,000, preferably between 5,000 and 30,000, although it may be as high as 1,000,000 ore more. An example of such a polysiloxane is as follows:

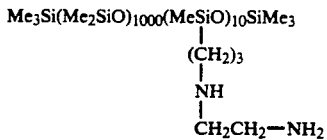

Particularly preferred are compositions in which the organosiloxane polymer has an average molecular weight in the ranges above. As indicated earlier, the silicones may be incorporated into dentifrices as silicone oils (and then emulsified in the dentifrice) or as silicone emulsions, preferably as emulsions. The sarcosine surfactants, nonionic surfactants and/or cationic surfactants may be used as emulsifiers. Certain cationic quarternary ammonium surfactants such as tallow trimethyl-ammonium chloride and cetyl pyridinium chloride are also considered antimicrobials.

The amines of the invention become protonated and bear positive charges when the pH is below their pKas. Depending on structure, the pKas will range from about 7 to about 12. The pH of the dentifrices including the silicones of the invention should be below 10 and are preferably between 6 and 8 so that the aminoalkyl groups are protonated.

The preferred dentifrices are toothpaste creams and gels and mouthwashes. Ingredients which may be included in toothpastes and gels generally and which may be used in toothpaste and gel compositions in accordance with the invention are abrasive polishing materials, sudsing agents, flavoring agents, hymectants, binders, sweetening agents, alcohol and water. Antitartar agents may be added to enhance the anticalculus affect of the present compositions.

Abrasives include alumina and hydrates thereof, such as alpha alumina trihydrate, magnesium trisilicate, magnesium carbonate, aluminosilicates, such as calcined aluminum silicate and aluminum silicate, calcium carbonate, zirconium silicate, polymethylmethacrylate, powdered polyethylene, silica and the like. Depending on the form which the dentifrice is to take, the abrasive may be present in an amount of from 0 to 70% by weight, preferably from 1 to 70%, more preferably from 10 to 70% for toothpastes.

Humectants contemplated for use in the present invention include glycerol, polyol, sorbitol, polyethylene glycols and propylene glycol. The humectants are generally present in amounts of from 0 to 80%, preferably from 1 to 70%, more preferably 5 to 70%, by weight. Thickeners suitable for use in the invention include silica. Thickeners may be present in toothpastes, creams and gels at 0.1 to 20% by weight. Binders suitable for use in the dentifrices of the invention include hydroxy ethyl cellulose (Natrasol), hydroxypropyl cellulose (Klucel) and lauryl cellulose ethers such as the experimental gum WSP M-1017 (ex Hercules). It is preferred that anionic binders be avoided as it is believed that they complex with the amine cations of the aminoalkyl silicone. Binders my be present in the toothpaste of the invention to the extent of from 0.01 to 3% by weight. Sweeteners suitable for use in the present dentifrice, preferably at levels of about 0.1% to 5%, include saccharin. Ethanol may be used in the present dentifrices, preferably at levels of 0 to 5%, particularly 0.5 to 5%, especially 0.5 to 3%.

Certain pyrophosphate and other polyphosphate salts have been disclosed in U.S. Pat. Nos. 4,515,772 and 4,627,977 as being useful as antitartar agents. These include di- and tetra-alkali metal pyrophosphates wherein the alkali metals are preferably selected from the group consisting of sodium and potassium. Although phosphates are generally not favored as they tend to react with aminoalkyl silicones, inclusion of these antitartar agents may be appropriate in certain formulations in accordance with our invention. Zinc salts are disclosed as anticalculus agents in U.S. Pat. No. 4,100,269 and in U.S. Pat. Nos. 4,416,867, 4,425,325 and 4,339,432 (with glycine). These antitartar agents may be included in the present formulations.

Surfactants other than the sarcosine surfactants may be included. However, it is generally preferred that surfactants (sudsing agents) other than sarcosine surfactants, used in the dentifrice of the invention be nonionic or cationic. Surfactants include polyoxypropylene-polyoxyethylene block copolymer, sorbitan stearate, sorbitan oleate, polysorbates, nonoxynols, dimethyl cocamine oxide, dimethyl lauryl amine oxide and monolauryl citrate esters. Total surfactant content (including sarcosine surfactant) may be present within the range of up to 15%, preferably 0.1 to 10%, more preferably 0.5 to 3% especially 0.5 to 1.5 by weight of the composition. Generally nonionic sudsing agents which may be suitable include condensation products of alkylene oxide groups with hydrophobic organic compounds such as alkyl phenols or the reaction products of propylene oxide and ethylene oxide diamine. Also included are the reaction products of ethylene oxide with aliphatic alcohols and long chain tertiary dialkyl sulfoxides. The cationic surfactants may be quaternary ammonium compounds including one $C_8$–$C_{18}$ alkyl chain. Examples include cetyl pyridinium chloride, cetyl trimethyl ammonium bromide, di isobutyl phenoxy ethoxy ethyl-dimethyl benzyl ammonium chloride and coconut alkyl trimethyl ammonium nitrate.

Flavors are usually included in dentrifices in low amounts of e.g., 0.10% to 3%. Any type of flavor may be used. However, low- and nonaldehydic flavors are generally preferred since the amines of the silicones may otherwise react with the acyl groups of the aldehyde to form Schiff bases, which are colored and which would make the nitrogen atoms on the silicones unavailable for interaction with the surface of the tooth.

Fluoride sources used in toothpastes such as sodium fluoride, stannous fluoride, zinc ammonium fluoride, tin ammonium fluoride, calcium fluoride and cobalt ammonium fluoride may be included. Sodium monofluorophosphate may also be used although it is not preferred as it tends to decrease the deposition of the silicone. Fluoride ions are typically provided at a level of from 50 to 1500 ppm, although higher levels up to, say, 3000 ppm may be used in the present dentifrices. Casein and its hydrolysate are other potential anticaries agents, e.g., at a level of 0.1 to 5% by weight.

Titanium dioxide is a suitable whitener.

Dyes/colorants suitable for dentrifices e.g., FD&C Blue #1, D&C Yellow #10, FD&C Red #40, etc. may be used in the present compositions.

Ingredients mentioned above as suitable for toothpastes are generally suitable for creams and gels, as will be apparent to one of skill in the art of toothpaste and gel formulation. Thus, except where otherwise noted, references to toothpastes are to be construed as applying to creams and gels as well.

The toothpastes of the invention are typically made by forming a premix of the gum, humectant and water, forming a premix of all the powders and adding it to the gum premix, mixing, adding flavor, preparing a silicone emulsion including the silicone, sarcosine surfactant and water, adding the emulsion to the paste and adjusting the pH with HCl and water.

Typically, mouthwashes comprise a water/alcohol solution, flavor, humectant, sweetener, sudsing agent, and colorant. The corresponding compounds mentioned above which are used in toothpastes, are generally suitable within the ranges above for mouthwashes as well. The mouthwash can include ethanol at a level of from 0 to 30% preferably from 0.5 to 30%. Nonionic and cationic surfactants are preferred.

Where chlorhexidine or another antimicrobial compound (or combination thereof) is included in the dentifrice of the invention, the preferred concentration may range from 0.001% to 3%. Especially preferred concentrations range from 0.1% to 1%. Cetylpyridmium chloride, phenolics such as DP300® exCiba Geigy and salicylamides (including salicylanilides), and sources of metal ions such as zinc, copper, silver and stanneous (e.g., zinc, copper and stanneous chloride, and silver nitrate) may also be appropriate antibacterial agents.

With the exception of the ethyoxylated and propoxylated compounds discussed below, the aminoalkylsilicone compounds are for the most part known. Methods of preparing aminoalkylsilicones are given in, for example, Jet et al., U.S. Pat. Nos. 2,930,809 including U.S. application Ser. Nos. 555,201 (filed Dec. 23, 1955), and 555,203 (Filed Dec. 23, 1955), all of which are hereby incorporated by reference.

The aminoalkyl polysiloxanes of the invention may be end capped. If end capped, one or more of the end capping groups, $R_e$, preferably include one or more nitrogen atoms. For example, $R_e$ may be $-(CH_2)_3NH_2$ or $-(CH_2)_3NHCH_2CH_2NH_2$.

As indicated above, a preferred class of aminoalkyl polysiloxanes is that of the amodimethicones. Amodimethicones are polydimethyl siloxane polymers containing aminoalkyl groups. The aminoalkyl groups may be, for example, n-propylamine or n-propyl-N-ethylenediamine and these may be present either pendent or at one or more ends of the polydimethylsiloxane chain. The amine groups cause the amodimethicone polymer to develop a net positive charge in aqueous systems over a wide range of pH say, from pH 1 to 10. Amodimethicones are commercially available, Examples of amodimethicones include Dow Corning's DC-929, DC-Q2-7224, and Q2-8075. Q2-8075 comprises aminoalkyl groups affixed to a predominantly polydimethyl siloxane structure. The typical structure of its aminoalkyl group containing units is:

The amodimethicones useful in the present invention are exemplified by the formula shown in Formula 5, below:

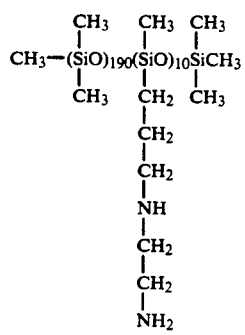

FORMULA 5

A special class of aminosilicones are ethoxylated and propoxylated aminosilicone compounds such as the following ethoxylated compound:

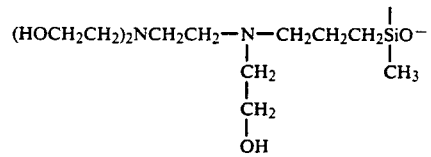

These have less of a tendency to react with aldehyde flavorants due to the presence of hydroxypropyl and hydroxyethyl groups. These compounds are described more fully in Lin et al. U.S. Pat application Ser. No. 276,719 and Ser. No. 276,726 entitled "Dentifrices Including Modified Aminoalkyl Silicones" and "Hydroxylhydrocarbyl-modified Amino Alkyl Silicones" filed simultaneously herewith and incorporated by reference hereby.

Unless otherwise specified or required by the context, percentages of ingredients are by weight.

The following specific examples further illustrate the invention, but the invention is not limited thereto.

EXAMPLE 1

Since an important goal of the invention is to render surfaces of the teeth hydrophobic and corrosion resistant, the hydrophobicity imparted to surfaces by structurally different silicone polymers was investigated. Acid-cleaned, glass cover slips were incubated in whole human saliva to develop a pellicle thereon. After incubation, the cover slips were rinsed with distilled water and placed into a 3% silicone emulsion for 30 seconds. The cover slips were then rinsed with distilled water and contact angle measurements of water droplets on the slips were obtained with a goniometer. The contact angle between a surface and a water droplet is an indication of the hydrophobicity of the surface: the higher the contact angle the more hydrophobic the surface. The results obtained are given in Table I.

TABLE I

| Silicone Polymer | Molecular Weight | Viscosity | Mean Contact Angle (degrees) | Amine Content (wt %) |
|---|---|---|---|---|
| Dimethicones: | 6,600 | 100 cs | 22 | — |
|  | 19,000 | 500 cs | 19 | — |
|  | 26,000 | 1,000 cs | 10 | — |
| Amodimethicones: | 6,000 | 0.096 | 56 | 0.6% |
|  | *12,000 | (intrinsic) | 71 |  |
|  | 15,000 | 0.128 | 55 | 0.29% |
|  | *18,000 | (intrinsic) | 75 |  |
|  | 22,000 | 0.22 | 54 | 0.15% |
|  | *42,000 | (intrinsic) | 75 |  |
| Dow Corning 929 |  |  | 57 |  |

*end capped with methoxy and N-2-aminoethyl-3-aminopropyl groups.

Since all of the oils investigated possessed a polydimethylsiloxane backbone, their inherent hydrophobicity would be expected to be similar. The foregoing data demonstrates that alkylamino silicones create a more hydrophobic surface, as compared to non amino-containing polysiloxanes. The data supports the concept that amino-functional groups increase the substantivity, i.e., affinity, of silicone based polymers.

EXAMPLE 2

Experiments were conducted to demonstrate that coating enamel with a substantive hydrophobic silicone film causes the enamel to be more resistant to attach from the organic acids produced by plaque bacteria and, therefore, to caries.

PROCEDURES

Bovine incisors were cut, ground and polished so as to decrease enamel surface variables. A standard area (approx. 40 mm$^2$) was masked off and the teeth were painted. Upon removal of the mask, the exposed enamel surfaces were brushed with a 0.5% Triton X-100 solution to remove residual adhesive. All the teeth were rinsed and stored in distilled, deionized water until treated.

Emulsions were prepared containing 35% of the respective silicone polymer (See Table 2) and 6.9% Tergitol NP-10. These were diluted with distilled water to yield a final concentration of 3% silicone oil. Treatments consisted of a 1 minute brushing and a 9 minute soaking in the 3% silicone emulsions followed by a 10 second rinse with distilled water.

Treated teeth were placed into a 0.1M lactic acid buffer, pH 4.5, at 37° C. and shaken at 200 rpm. Aliquots of the buffer were removed at different time intervals up to 30 minutes and assayed for phosphorus using the Chen assay for the microdetermination of phosphorus in accordance with "Official Methods of Analysis, Association of Official Analytical Chemists," edited by Sidney Williams, Arlington, Va. p. 632. Percent reductions in acid dissolution rate were calculated by comparing the silicone-treated teeth to a water treated control set. The results are set forth in Table 2.

TABLE 2
ACID DISSOLUTION RESULTS OF SILICONE-TREATED BOVINE TEETH

| Silcone Polymer | | Molecular Weight | % Reduction in Acid Dissolution | Mole % Alkylamide |
|---|---|---|---|---|
| Dimethicones: | | | | |
| Union Carbide | LE-474 | 12,000 | 4.46 | 0.0 |
| | LE-460 | 28,000 | 9.85 | 0.0 |
| SWS Silicones | 100 cs | 6,600 | 15.0 | 0.0 |
| SWS Silicones | 500 cs | 19,000 | 5.2 | 0.0 |
| Petrach Sys. | 1000 cs | 26,000 | 6.6 | 0.0 |
| Amodimethicones: | | | | |
| (endcapped with methoxyl group | | 12,000 | 27.3 | 2.5 |
| (endcapped with methoxyl group) | | 18,000 | 25.6 | 1.6 |
| (endcapped with hydroxyl group) | | | 33.3 | low |
| Endcapped, R$^1$ | | 6,000 | 25.0 | 2.5 |
| | | 15,000 | 21.3 | 1.0 |
| | | 22,000 | 16.0 | 0.7 |
| Endcapped, R$^2$ | | 19,000 | 24.2 | 0.8 |
| | | 28,000 | 28.0 | 0.7 |
| Pendant, R$^1$ | | 5,000 | 57.7 | 9.5 |
| | | 15,000 | 47.9 | 3.0 |
| | | 25,000 | 36.6 | 1.8 |
| Pendant, R$^2$ | | 25,000 | 39.8 | 1.8 |
| R$^2$ = n-propylamine | | | | |
| R$^1$ = n-propyl-N-ethylenediamine | | | | |
| Dow Corning | | 929 (pendant amines hydroxyl end groups) | 25.7 | low |
| | | Q2-7224 | 10.4 | 2.0 |
| | | Q2-8075 | 28.7 | 2.0 |
| Compound of Formula 5 (p. 22) | | 15,000 mw | 74.2 | 5.0 |

DIMETHICONE (POLYDIMETHYLSILOXANE)

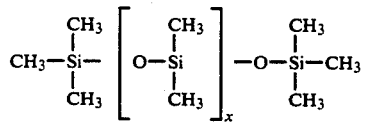

AMODIMETHICONES, END CAPPED

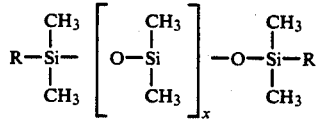

AMODIMETHICONE, PENDANT

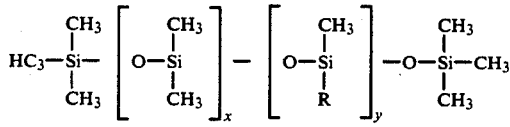

For R$^1$, R = —CH$_2$CH$_2$CH$_2$NH$_2$

TABLE 2-continued

For $R^2$, $R = -CH_2CH_2CH_2NHCH_2CH_2NH_2$

The contact angle data of Example I showed amodimethicones to impart a higher degree of hydrophobicity to a pellicle-coated surface than dimethicones. The acid dissolution data of the present example demonstrates the effectiveness of amino-functional silicones are alkyl silicones in depositing onto an enamel surface and in protecting it from caries.

Within the class of amodimethicones, it appears that those polymers having pendant alkylamines are more substantive to enamel and provide a better protective film than those having endcapping alkylamines. This increase in efficacy appears to be due to an overall increase in amine content (i.e., points for attachment). Indeed, the amodimethicones show a correlation between percent alkylamine and ability to reduce dissolution. Within the ranges of % alkylamine shown, an increase in alkylamine content tends to increase the % reduction in acid dissolution.

In the silicones with methoxy end caps, the methoxy group may further lend to the polymer's attachment to enamel through a covalent linkage thereby increasing polymer substantivity. The DC-929 is a commercially available emulsion of a polyalkyl silicone having low pendant amine content and hydroxyl endgroups. Hydroxyl endgroups may also enhance deposition in a manner similar to that of the methoxyl groups.

As a class, aminoalkyl silicones are more substantive to enamel than dimethicones. The most substantive amino silicone polymers are those which posses more than 3% alkylamine, pendantly attached to the polydimethylsiloxane backbone.

EXAMPLE 3-5

Reaction

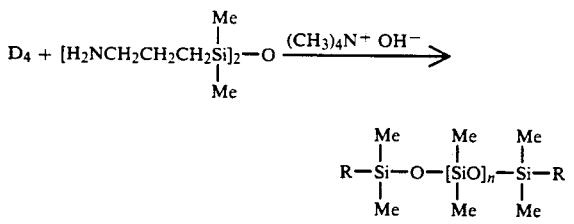

where $R = -(CH_2)_3NH_2$

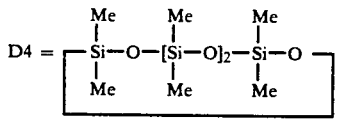

Reaction

Into a 2 liter resin kettle equipped with mechanical stirrer (through a water-cooled joint), water condenser with argon inlet, and an additional funnel, was placed 1 kg of (SWS-03314) (ex. SWS Company, of Stauffer Chemical Company). It was stirred under a light argon flow to remove any air or moisture. 5.25 g of tetramethylammonium hydroxide (ex Aldrich) was added as the catalyst. 50.50 ml (45.3 g) of 1,3-Bis(3-aminopropyl-1,1, 3,3-tetramethyldisiloxane (Petrarch, Silar) was added dropwise to the mixture. The contents were heated at 95-100° C. for 20 hours and 2 hours at 150° C. The heating mantle wan then removed and the mixture was allowed to cool to room temperature with stirring, under argon.

In order to remove excess amine and volatile components, the product was put on the rotary evaporator using vacuum first at room temperature and then heating to 85° C. for about an hour.

Characterization

Bulk viscosity was measured to be 100 centistokes using a Brookfiled viscometer. Intrinsic viscosity of solutions of the polymer in toluene were determined using an Ostwald tube and found to be 0.0605 dl/g.

Molecular weight was found by the Mark-Houwink equation, "n]$=KM^a$, where a$=0.66$ and K$=2\times10^{-4}$ for silicone polymers, to be 6000.

EXAMPLE 4: (MW 15000)

1043 g of D4, 5.3 g of tetramethylammonium hydroxide and 15.71 g of 1,3-Bis(3-aminopropyl)-1,1,3, 3-tetramethylsiloxane were reacted together at 95-110° C., as described in Example 3. Vacuum was used to purify the polymer product. Characterization procedures were the same as in Example 3. Bulk viscosity was 430 centistokes, intrinsic viscosity was 0.1155 dl/g, and MW was 15000.

EXAMPLE 5: (MW 22000)

1021 g of D4, 5.25 g of tetramethylammonium hydroxide, and 9.23 g of 1,3-Bis(3-aminopropyl)-1,1,3,3-tetramethylsiloxane were reacted together at 95-100° C., followed by catalyst decomposition, as described in Example 3. The rotary evaporator was used to purify the product. Characterization procedures were the same as in example 3. The bulk viscosity was 1040 centistokes, the intrinsic viscosity was 0.1485 dl/g, and MW was 22000.

EXAMPLE 6

Siloxanes containing pendant amines (MW 5000)

a) Synthesis of cyclic siloxanes containing amines

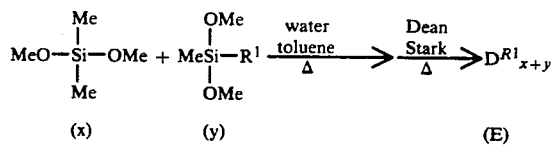

$R^1 = (CH_2)_3NH(CH_2)_2NH_2$

Into a 2 liter resin kettle equipped with mechanical stirrer, water condenser with argon inlet and addition funnel, was placed 350 g (x; 2.91 moles) of dimethyldimethoxysilane (Petrarch). Toluene (220 mls) was used as the solvent. 275.0 g (y; 1.33 moles) of aminoethylaminopropylmethyldimethoxysilane (Petrarch) was added followed by 2(x+y) moles Millipore water (152.6 g). The reaction was quite exothermic. When it cooled, it was heated at reflux temperature (71° C.) for 18½ hours. The Dean Stark condenser was used to remove the reaction by-products and solvents, and to drive the reaction to completion. A rotary evaporator was used to remove the rest of the toluene. A viscous slightly orange colored fluid was isolated as the product, (E). A 60 MH$_2$ NMR spectrum was used to determine the amount of amine present in the cyclic product, to be 1.1 amine group (R$^1$) per D$_3$ unit (or D$_4^{1.45}$R$^2$ in terms of D$_4$ for simplicity).

b) Preparation of 5000 MW siloxane with pendant amines

Reaction

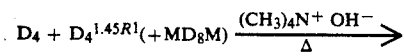

(E)

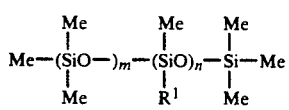

where R$^1$ = (CH$_2$)$_3$NH(CH$_2$)$_2$NH$_2$ where R$^1$ = (CH$_2$)$_3$NH(CH$_2$)$_2$NH$_2$ Into a 2 liter resin kettle, equipped with water condenser, argon inlet, mechanical stirrer, addition funnel, and thermometer, was placed 380 g D$_4$(SWS), and 167.8 g D$_4^{1.451}$ "(E) from part a]. 3.11 g MD$_8$M (Dow Corning 200-5 cs fluid) where M=Me$_3$Si$_{0.5}$ and D=Me$_2$Si-O as end capper and tetramethylammonium hydroxide (Aldrich) were added. The reaction mixture was heated at 95° C. for 19 hours and then at 155° C. for 3 hours. Rotary evaporation removed the excess materials. The polymer was filtered to remove particulates.

Characterization of the polymer included measuring bulk viscosities using a Brookfield viscometer. The bulk viscosity was 120 cs. Since the viscosity-MW equations hold for siloxanes, but may not hold the siloxanes containing pendant amines, the MW was estimated from the stoichiometry of the reaction. The MW is approximately 5000, taking into account that this is an equilibrium polymerization with 10% excess volatile silicone before rotary evaporating. There are, on average, 6 pendant amines (R$^1$) per polymer.

EXAMPLE 7: SILOXANES CONTAINING PENDANT AMINES (MW 25000) (R=CH$_2$CH$_2$CH$_2$NH$_2$)

1035 g D$_4$, 62.2 g D$_4^{1.45R}$, 5.6 g of tetramethylammonium hyroxide catalyst, and 30.1 g of the MD$_8$M endcapper were reacted together at 100° C. for 16 hours 150° C. for 2 hours and subjected to rotary evaporation. Bulk viscosity was found to be 540 cs. MW was estimated at 25000, with 6 pendant amines (R) per polymer.

TABLE 6
Compounds for Exs. 8-26

| Trade Name | Chemical Name | Supplier |
|---|---|---|
| Natrosol 250M | Hydroxyethylcellulose (nonionic water soluble polymer) (Gum/Binder) | Hercules Inc. Wilmington, DE |
| Hercules WSP M-1017 | Experimental (Lauryl Cellulose Ether) (Gum/Binder) | Hercules Inc. Wilmington, DE |
| Celcoloid-S | Propylene Glycol Alginate (Gum/Binder) | Kelco, Clark, NJ |
| Polyol III | A mixture of sorbitol and hydrogenated corn syrup (Gum/Binder) | Lonza, Roquette Corporation |
| Alumina 331 | Hydrated Alumina (Al$_2$O$_3$) (Abrasive) | Aluchem, Alcoa |
| Pluronic F-87 | Polyoxy Propylene Polyoxyethylene Block Copolymer (Surfactant) | BASF-Wyandotte, Parsippany, NJ |
| Arlacel-80 | Sorbitan Oleate (Surfactant) | ICI Americas |
| Tween-80 | Polysorbate-80 (Surfactant) | ICI Americas |
| Tween-60 | Polysorbate-60 (Surfactant) | ICI Americas |
| Tergitol NP-15 | Nonoxynol-15 [Polyoxyethylene(15)Nonyl Phenyl Ether] (Surfactant) | Union Carbide |
| Titanium Dioxide | — (Whitener) | Whitaker, Clark & Daniels |
| Flavor | — (Flavor) | International Flavors & Fragrances (IFF) |
| Lauramine Oxide | Dimethylcocoamine Oxide (Surfactant) | Armak Industrial Chem. Div. |
| Cocoamine Oxide | | |
| PEG 1450 | Polyethyleneglycol (mw 1450) (Humectant) | Union Carbide |
| Syloid 63X | Hydrated Silica (SiO$_2$) (Abrasive) | W. R. Grace & Co. |
| Syloid 244 | Hydrated Silica (SiO$_2$) (Thickener) | W. R. Grace & Co. |
| Hamposyl C-30 | Sodium Cocoylsarcosinate (30% w/w solution) (Surfactant) | W. R. Grace & Co. |
| Hamposyl L-30 | Sodium Lauroylsarcosinate (30% w/w solution) (Surfactant) | W. R. Grace & Co. |
| Hamposyl L-95 | Sodium Lauroylsarcosinate (95% active) (Surfactant) | W. R. Grace & Co. |
| Ammonyx DMCD-40 | Dimethylcocoamine oxide (40% active) (Surfactant) | Onyx Chemical Co. |
| Chlorhexidine Digluconate | Chlorhexidine digluconate (20% w/w solution) (Active) | Lonza |
| Perillartine | — (Sweetener) | Takasago Corp. |
| Flavor 2540 | — (Flavor) | Formulated in house |
| Flavor 77171 | — (Flavor) | Int'l Flavors & Fragrances |
| Aspartame | N-L-α-Aspartyl-L-phenylalanine-1-methyl ester (Sweetener) | Nutrasweet Co. |
| Saccharin | Sodium Saccharin (Sweetener) | |

EXAMPLES 8-26

Toothpaste formulations were prepared by mixing the listed ingredients together. The toothpaste formulations were tested for reduction of acid dissolution as in Example 2. Results are given below.

| | SILICONE POLYMER DENTIFRICE FORMULATIONS | | | | | | | |
|---|---|---|---|---|---|---|---|---|
| | PARTS BY WEIGHT | | | | | | | |
| Ingredients | Ex. 8 | Ex. 9 | Ex. 10 | Ex. 11 | Ex. 12 | Ex. 13 | Ex. 14 | Ex. 15 |
| Natrosol 250M | 1.25 | 1.25 | 1.25 | 1.00 | 1.00 | 1.10 | 1.25 | 1.00 |
| Glycerin | 27.00 | 27.00 | 27.00 | 27.00 | 27.00 | 13.50 | 13.50 | 27.00 |
| Polyol III | — | — | — | — | — | 13.50 | 13.50 | — |
| Alumina 401 | 50.00 | 50.00 | 50.00 | 50.00 | 50.00 | 50.00 | 50.00 | 50.00 |
| Titanium Dioxide | 0.50 | 0.50 | 0.50 | 0.50 | 0.50 | 0.50 | 0.50 | 0.50 |

-continued

| SILICONE POLYMER DENTIFRICE FORMULATIONS | | | | | | | | |
|---|---|---|---|---|---|---|---|---|
| Silicone Oil of FIG. 5 | 4.00 | 4.00 | 2.00 | 2.00 | 2.00 | 1.00 | 1.00 | 1.50 |
| Hamposyl C-30 (30% active) | — | — | — | — | — | 3.33 | — | — |
| Hamposyl L-30 (30% active) | — | — | — | 2.00 | — | — | 1.66 | 2.00 |
| Aromox DMMC-W (40% active) | 2.00 | — | 1.00 | — | 2.00 | — | — | — |
| Arlacel 60 | — | 1.13 | — | — | — | — | — | — |
| Tween 60 | — | 1.37 | — | — | — | — | — | — |
| Chlorhexidine Digluconate (20% solution) | 4.00 | — | 4.00 | 4.00 | 4.00 | — | — | 4.00 |
| Sodium Fluoride | 0.10 | — | 0.10 | 0.20 | 0.20 | 0.20 | 0.20 | 0.20 |
| Aspartame | 0.30 | 0.30 | — | — | — | 0.30 | — | — |
| Perillartine | — | — | — | 0.10 | 0.10 | — | — | 0.10 |
| Sodium Saccharin | — | — | — | — | — | — | 0.20 | — |
| Flavor 2540 | 1.00 | — | — | 1.00 | 1.00 | 1.00 | 0.80 | 1.00 |
| Flavor 77171 | — | 1.00 | 1.00 | — | — | — | — | — |
| Distilled Water | 9.85 | 13.45 | 13.15 | 12.20 | 12.20 | 15.17 | 14.59 | 12.70 |
| 1M Acetic Acid | — | — | — | — | — | 2.90 | 2.80 | — |
| 1M HCl | — | — | — | — | — | — | — | — |
| pH | | | | 9.9 | | 7.32 | 7.24 | 9.71 |
| % Red. in Acid Diss. | 71.30 | 55.30 | 21.10 | 99.50 | 54.70 | 31.50 | 29.90 | 98.50 |

| Ingredients | PARTS BY WEIGHT | | | | | |
|---|---|---|---|---|---|---|
| | Ex. 16 | Ex. 17 | Ex. 18 | Ex. 19 | Ex. 20 | Ex. 21 |
| Natrosol 250M | 1.00 | 1.00 | 1.00 | 1.10 | 1.10 | 1.10 |
| Glycerin | 27.00 | 27.00 | 27.00 | 27.00 | 27.00 | 27.00 |
| Alumina 401 | 50.00 | 50.00 | 50.00 | 50.00 | 50.00 | 50.00 |
| Titanium Dioxide | 0.50 | 0.50 | 0.50 | 0.50 | 0.50 | 0.50 |
| Silicone Oil of FIG. 5 | 1.00 | 1.00 | 2.00 | 2.00 | 2.00 | 4.00 |
| Hamposyl C-30 (30% active) | — | — | — | 2.00 | — | — |
| Hamposyl L-30 (30% active) | 2.00 | 2.00 | 2.00 | — | 3.33 | — |
| Hamposyl L-95 (95% active) | — | — | — | — | — | 0.50 |
| Chlorhexidine Digluconate (20% solution) | 4.00 | 4.00 | — | — | — | — |
| Sodium Fluoride | 0.20 | 0.20 | 0.20 | 0.20 | 0.20 | 0.20 |
| Perillartine | 0.10 | 0.10 | — | — | — | — |
| Sodium Saccharin | — | — | 0.20 | 0.20 | 0.20 | 0.20 |
| Flavor 2540 | 1.00 | 1.00 | 1.00 | 1.00 | 1.00 | 1.00 |
| Distilled Water | 11.20 | 13.20 | 14.10 | 15.00 | 13.67 | 14.50 |
| 1M Acetic Acid | 2.00 | — | — | — | — | — |
| 1M HCl | — | — | 2.00 | — | — | — |
| 2M HCl | — | — | 1.00 | 1.50 | 2.10 | 2.00 |
| pH | 7.66 | | 7.75 | 7.66 | 7.30 | 7.51 |
| % Red. in Acid Diss. | 98.00 | 99.00 | 20.90 | 49.50 | 38.40 | 52.00 |

| Ingredients | PARTS BY WEIGHT | | | |
|---|---|---|---|---|
| | Ex. 22 | Ex. 23 | Ex. 24 | Ex. 25 |
| Natrosol 250M | 1.00 | 1.10 | 1.10 | 1.10 |
| Glycerin | 27.00 | 27.00 | 27.00 | 27.00 |
| PEG 1450 | — | 5.00 | — | 5.00 |
| Syloid 63X | 26.00 | 14.00 | 14.00 | 14.00 |
| Syloid 244 | 11.40 | 8.00 | 8.00 | 8.00 |
| Titanium Dioxide | 0.50 | 0.50 | 0.50 | 0.50 |
| Silicone Oil of FIG. 5 | 2.00 | 2.00 | 2.00 | 2.00 |
| Hamposyl L-30 (30% active) | 2.00 | 2.00 | 2.00 | 2.00 |
| Sodium Fluoride | 0.20 | 0.20 | 0.20 | 0.22 |
| Perillartine | 0.10 | 0.10 | 0.10 | — |
| Sodium Saccharin | — | — | — | 0.30 |
| Flavor 2540 | 1.00 | 1.00 | 1.00 | 1.00 |
| Distilled Water | 26.70 | 39.10 | 44.10 | 38.88 |
| 2M HCl | — | — | — | — |
| pH | 7.17 | 7.78 | 7.53 | 7.77 |
| % Red. in Acid Diss. | 93.10 | 96.90 | 98.90 | 26.60 |

Examples 10, 11, 12 and 15 tend to demonstrate the superior results obtained when sarcosine surfactants are included in a dentifrice comprising amino alkyl silicone and chlorhexidine. Example 22, 23 and 24 demonstrate the excellent results which can be obtained when the silica abrasive is used.

EXAMPLES 26-27

Mouthrinses (Prophetic formulas)

EXAMPLE 26

| INGREDIENT | CONC. % |
|---|---|
| Amodimethicone of FIG. 5 | 1.00 |

-continued

| INGREDIENT | CONC. % |
|---|---|
| Sodium N-lauryl sarcosinate | 0.30 |
| Water | 45.84915 |
| 96% Glycerin USP | 50.00 |
| Ethanol | 2.00 |
| Flavor | 0.25 |
| D & C Yellow #10 | 0.00060 |
| FD & C Blue #1 | 0.00025 |
| 20% Chlorhexidine Digluconate (ex. Lonza Spectrodyne G.) | 0.60 |

The mouthwash is made by dissolving 0.2% sodium N-lauryl sarcosinate in water. The amodimethicone is then added and emulsified. The emulsions thus prepared are added to glycerin and mixed. 0.1% sodium N-lauryl sarcosinate in ethanol is then dissolved in the mixture, flavor is added to ethanol and mixed, then added to the above mixture. The colors are added and mixed. Finally, chlorhexidine is added and mixed.

| INGREDIENT | CONC. % |
|---|---|
| 70% Sorbitol Soln. | 50.00 |
| Water | 43.69915 |
| Amodimethicone of FIG. 5 | 1.00 |
| Sodium N-cocoyl sarcosinate | 0.39 |
| Water | 2.06 |
| Ethanol (200PF) | 2.00 |
| Flavor | 0.25 |
| D & C Yellow #10 | 0.00060 |
| FD & C Blue #1 | 0.00025 |
| 20% Chlorhexidine Digluconate (ex. Lonza Spectrodyne G.) | 0.60 |

The mouthwash is prepared as follows:

Sorbitol and water are mixed. The amodimethicone is emulsified with 0.09% tergitol and water and added to the sorbitol/water mixture. 0.30% tergitol is dissolved in ethanol and flavor is added. After mixing, the flavor mixture is added to the silicone emulsion. Colors are added and mixed. Finally, chlorhexidine is added and the preparation is mixed.

It should be understood that the specific forms of the invention herein illustrated and described are intended to be representative only. Changes, including but not limited to those suggested in this specification, may be made in the illustrated embodiments without departing form the clear teachings of the disclosures. Accordingly, reference should be made to the following appended claims in determining the full scope of the invention.

We claim:

1. A dentifrice comprising (a) an aminoalkyl silicone of a formula comprised of two basic units:

$$R^1_m R_n SiO_{(4-m-n)/2} \quad (1)$$

wherein $1 \leq m+n \leq 3$, $1 \leq n \leq 3$, $0 \leq m \leq 2$, and m and n are integers and $$R^1_a R^2_b SiO_{(4-a-b)/2} \quad (2)$$

wherein $1 \leq a+b \leq 3$, and a and b are integers wherein $R^1$ and $R^2$ are hydrocarbons or fluorinated hydrocarbons of 1 to 10 carbons, hydroxyl, alkoxyl, cyanoalkyl, hydrogen or acetoxy, and R is

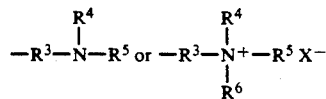

wherein $R^3$ is a divalent alkylene of 1-20 carbons or a hydrocarbon of 1-20 carbon atoms containing 0 atoms, $R^4$, $R^5$ and $R^6$ may be different or the same and are selected from the group consisting of H, hydrocarbons of 1-20 carbons, and hydrocarbons of 1-20 carbons containing N and/or O atoms, and $X^-$ is a monovalent anion, said aminoalkyl silicone including 60% or fewer by repeat unit of unit (1);
(b) an abrasive and (c) a sarcosine surfactant of the formula $RCON(CH_3)CH_2CO_2Q$ wherein R is a hydrocarbon group of 7 to 21 carbon atoms and Q is selected form the group consisting of alkali metal ions, ammonium ions and hydrogen.

2. The dentifrice according to claim 1 wherein the amino alkyl silicone is a block copolymer.

3. The dentifrice according to claim 1 wherein the amino alkyl silicone is a random copolymer.

4. The dentifrice according to claim 1 wherein the amino alkyl silicone is a linear copolymer.

5. The dentifrice according to claim 1 wherein $R^1$ and $R^2$ are each independently selected from the group consisting of methyl, ethyl, phenyl, vinyl, -trifluoropropyl or cyano.

6. The dentifrice according to claim 1 wherein $R^3$ is a divalent alkylene having from 3 to 5 carbon atoms.

7. The dentifrice according to claim 1 wherein R is selected from the group consisting of:

$$-(CH_2)_3-NH_2 \text{ and } -(CH_2)_3-NHCH_2CH_2NH_2,$$

8. Dentifrice of claim 1 wherein the dentifrice is a toothpaste, $R^1$ is methyl or ethyl, $R^2$ is methyl or ethyl and $R^3$ is a divalent alkylene having from 3 to 5 carbon atoms.

9. The dentifrice of claim 1 comprising by weight from 0.1 to 20% amino alkyl silicone, from 1 to 70% abrasive, from 1 to 80% humectant, from 0.1 to 3% binder, and 0.1 to 6% sarcosine surfactant, and from 50 to 3,000 ppm fluoride ion.

10. The dentifrice according to claim 9 wherein from 5 to 30% of the repeating units are unit (1).

11. The toothpaste according to claim 10 further comprising an orally acceptable antimicrobial agent.

12. The toothpaste according to claim 11 wherein the antimicrobial agent is chlorhexidine.

13. The dentifrice of claim 1 wherein the silicone has a molecular weight of 5,000 or above.

14. The dentifrice of claim 1 wherein the aminoalkyl silicone is an amodimethicone.

15. The dentifrice of claim 1 wherein from 5 to 30% of the repeating units are unit (1).

16. The dentifrice of claim 1 further comprising an orally acceptable antimicrobial agent in addition to the amino alkyl silicone and the sarcosinate.

17. The dentifrice of claim 16 wherein the antimicrobial agent is chlorhexidine.

18. A dentifrice which comprises a mixture of (I) an organosiloxane polymer which includes:
(a) at least one unit of the formula (3),

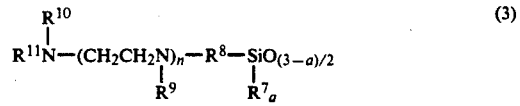

wherein:
a is from 0-2 and n is from 0-5,
$R^7$ is a monovalent radical,
$R^8$ is a divalent hydrocarbon radical,
$R^9$, $R^{10}$, and $R^{11}$ may be the same or different and are selected from the group consisting of $R^{12}$, where $R^{12}$ is a monovalent hydrocarbon or hydrogen, and
(b) at least one unit of the formula 4, $$R_a^{13}R_c^{14}SiO_{(4-a-c)/2} \quad (4)$$

wherein $R^{13}$ and $R^{14}$ are the same or different monovalent radicals, a and c are integers of the group selected from 0, 1, 2 and 3 and a plus c is 1, 2 or 3, (II) an orally acceptable antimicrobial compound, said organosiloxane polymer including 60% fewer by repeat units of unit (3);

(III) an abrasive and (IV) a sarcosine surfactant of the formula $RCON(CH_3)CH_2Q$ wherein R is a hydrocarbyl group of 7 to 21 carbon atoms and Q is selected from the group of alkali metal cations, ammonium ions and hydrogen.

19. The dentifrice of claim 18 wherein $R^7$ is selected from the group consisting of methyl, phenyl and -trifluoropropyl.

20. The dentifrice of claim 19 wherein $R^8$ comprises a divalent hydrocarbon radical having 3 or more carbon atoms.

21. The dentifrices of claim 18 wherein $R^{12}$ is selected from the group consisting of hydrogen, methyl or phenyl.

22. The dentifrice of claim 18 wherein $R^{13}$ and $R^{14}$ are independently selected from the group consisting of methyl, phenyl and -trifluoropropyl.

23. The dentifrice of claim 18 wherein the antimicrobial compound is chlorhexidine.

24. The dentifrice of claim 23 wherein the concentration of chlorhexidine is from 0.001% to 3%.

25. The dentifrice of claim 19 wherein the organosiloxane polymer has a molecular weight of between 5000 and 100,000.

26. The dentifrice of claim 19 wherein the organopolysiloxane includes from 5 to 30% by repeat unit of Formula (3).

27. A dentifrice which comprises a mixture of
(I) an organosiloxane polymer which includes:
(a) at least one unit of the formula (3),

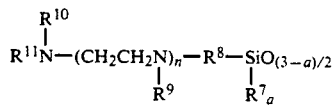

(3)

wherein:
a is from 0–2 and n is from 0–5,
$R^7$ is a monovalent radical,
$R^8$ is a divalent hydrocarbon radical,
$R^9$, $R^{10}$, and $R^{11}$ may be the same or different and are selected from the group consisting of $R^{12}$, where $R^{12}$ is a monovalent hydrocarbon or hydrogen, and
(b) at least one unit of the formula 4, $$R_a{}^{13}R_c{}^{14}SiO_{(4-a-c)/2} \quad (4)$$

wherein $R^{13}$ and $R^{14}$ are the same or different monovalent radicals, a and c are integers of the group selected from 0, 1, 2 and 3 and a plus c is 1, 2 or 3, said organosiloxane polymer including 60% or fewer by repeat units of unit (3) and (II) an orally acceptable antimicrobial compound:
(III) a humectant, and
(IV) a sarcosine surfactant of the formula $R^{15}CON(CH_3)CH_2CO_2Q$ wherein $R^{15}$ is a $C_7$ to $C_{21}$ hydrocarbyl
group and Q is selected from the group of alkali metal cations, ammonium ions and hydrogen.

28. The dentifrice of claim 1 wherein X is $Na^+$, $K^+$ or $NH_4{}^+$ and Q is $C_9$ to $C_{13}$.

29. The dentifrice of claim 19 wherein X is $Na^+$, $K^+$ or $NH_4{}^+$ and Q is $C_9$ to $C_{13}$.

30. The dentifrice of claim 27 wherein X is $Na^+$, $K^+$ or $NH_4{}^+$ and Q is $C_9$ to $C_{13}$.

31. The dentifrice of claim 21 wherein X is $Na^+$, $K^+$ or $NH_4{}^+$ and Q is $C_9$ to $C_{13}$.

32. The dentifrice of claim 27 where the dentifrice is a mouthwash.

33. The dentifrice of claim 1 further comprising stannous fluoride.

34. The dentifrice of claim 18 further comprising stannous fluoride.

35. The dentifrice of claim 27 further comprising stannous fluoride.

* * * * *